United States Patent [19]

Rapold et al.

[11] Patent Number: 5,384,403
[45] Date of Patent: Jan. 24, 1995

[54] PROCESS FOR THE PREPARATION OF AMINOTRIAZINE DERIVATIVES

[75] Inventors: Thomas Rapold, Kaisten; Marcel Senn, Rheinfelden, both of Switzerland

[73] Assignee: Ciba-Geigy Corporation, Ardsley, N.Y.

[21] Appl. No.: 194,185

[22] Filed: Feb. 9, 1994

Related U.S. Application Data

[63] Continuation-in-part of Ser. No. 40,691, Mar. 31, 1993, abandoned.

[51] Int. Cl.$^6$ .................. C07D 253/08; C07D 253/06
[52] U.S. Cl. ...................................... 544/182; 544/183
[58] Field of Search ............................... 544/182, 183

[56] References Cited

U.S. PATENT DOCUMENTS

| | | | |
|---|---|---|---|
| 4,931,439 | 6/1990 | Kristinsson | 544/182 |
| 4,996,325 | 2/1991 | Kristinsson | 548/132 |

FOREIGN PATENT DOCUMENTS 0433218  6/1991  European Pat. Off. .

*Primary Examiner*—John M. Ford
*Attorney, Agent, or Firm*—Marla J. Mathias

[57] ABSTRACT

The present invention relates to a process for the preparation of aminotriazine derivatives of the formula I

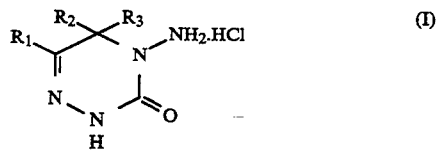

by the solvolysis of compounds of the formula II

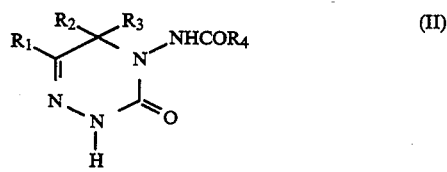

in the presence of gaseous hydrogen chloride in an alcoholic medium.

The compounds of formula I are useful as intermediates in the manufacture of insecticides.

4 Claims, No Drawings

PROCESS FOR THE PREPARATION OF AMINOTRIAZINE DERIVATIVES

This is a continuation-in-part of application Ser. No. 08/040,691, filed Mar. 31, 1993, now abandoned.

The present invention relates to a process for the preparation of aminotriazine derivatives of the formula I

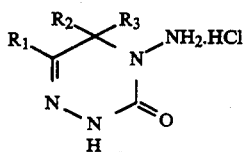
(I)

by the solvolysis of compounds of the formula II

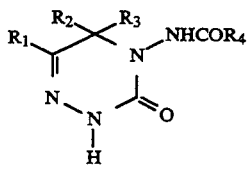
(II)

in the presence of gaseous hydrogen chloride in an alcoholic medium.

The compounds of formula I are useful intermediates in the manufacture of agrochemicals, particularly insecticides, as described in EP-A-0 314 615.

A process for the preparation of aminotriazine derivatives is described in EP-A-0 433 218 in which compounds of formula II above are converted to compounds of formula I by acidification and cleavage of the —COR$_4$ group as carboxylic acid in the presence of aqueous HCl.

Disadvantages of known processes, including that described in EP-A-0 433 218, are unsatisfactory product and volume yields for efficient industrial scale production, and instability of the end product in the reaction mixture. A further shortcoming of known processes is the establishment of an equilibrium state which cannot be shifted adequately to the product side so that the reaction remains essentially incomplete.

Surprisingly it has now been found that a substantial increase in product yield and purity, and a shift in the equilibrium state is obtained by replacing aqueous hydrochloric acid by hydrogen chloride gas. Furthermore the decomposition of the end product in the reaction medium is prevented.

It is the object, therefore, of the present invention to provide a process for the preparation of 4-amino-3-oxo-2,3,4,5-tetrahydro-1,2,4-triazine derivatives of the formula I

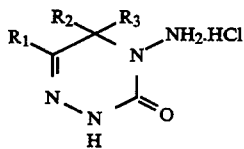
(I)

wherein R$_1$ is hydrogen, C$_1$-C$_{12}$alkyl, C$_3$-C$_6$cycloalkyl, C$_1$-C$_4$alkoxy-C$_1$-C$_6$alkyl, C$_1$-C$_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, C$_1$-C$_5$alkyl, C$_1$-C$_2$haloalkyl, methoxy and/or ethoxy; R$_2$ is hydrogen, C$_1$-C$_6$alkyl or C$_3$-C$_6$cycloalkyl, or is phenyl that is unsubstituted or substituted by C$_1$-C$_{12}$alkyl, halogen or by C$_1$-C$_{12}$ haloalkyl, or R$_1$ and R$_2$ together form a saturated or unsaturated 3- to 7-membered carbocycle, and R$_3$ is hydrogen or C$_1$-C$_6$alkyl, by the solvolysis of compounds of the formula II

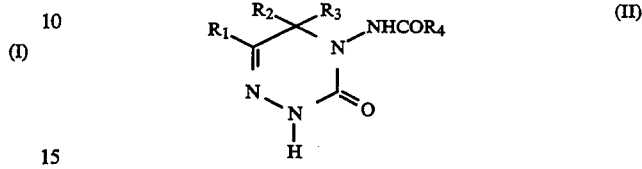
(II)

wherein R$_4$ is H, C$_1$-C$_4$-alkyl, C$_3$-C$_6$-cycloalkyl, C$_1$-C$_4$-alkyl substituted by 1 to 9 chlorine atoms, C$_1$-C$_3$-alkoxy, C$_1$-C$_3$-alkylthio, phenyl, pyridyl, or phenyl or pyridyl which is substituted with 1 to 3 substituents selected from the group of halogen, methyl, ethyl, methoxy, methylthio or nitro, in the presence of gaseous hydrogen chloride in an alcoholic medium.

The compounds of formula I may be converted directly into the free amines, for example by alkaline hydrolysis after completion of the reaction.

R$_1$ is preferably methyl or ethyl, and more preferably methyl. R$_2$ is preferably H or C$_1$-C$_4$alkyl, and more preferably H, methyl or ethyl. R$_3$ is preferably H or C$_1$-C$_4$alkyl, and more preferably H or methyl. R$_4$ is preferably H or C$_1$-C$_4$-alkyl, and more preferably methyl or ethyl.

The alcoholic medium can consist of one or more primary, secondary or tertiary alcohols. Examples are methanol, ethanol, n-propanol, isopropanol, n-butanol, n-pentanol or a mixture of these. Methanol is preferred.

The reaction medium can be anhydrous or contain very small amounts of water so that the water content can be between 0 and 5 weight-% with respect to the acetyltriazinone of formula II. Substantially dry conditions, i.e. 0 to 3 wt-% water content are preferred, more preferably 0 to 2 wt-% with respect to the acetyltriazinone of formula II. Anhydrous conditions, i.e. 0 wt-% water content, are particularly preferred.

The reaction can be conducted at a temperature between 0° C. and the boiling point of the solvent used. The preferred temperature range is 40° to 50° C.

Dry HCl gas is bubbled into the reaction mixture and unreacted HCl is recycled. The reaction conditions remain non-corrosive to the reaction vessel on account of the zero or very low water content.

The process according to the invention can be conducted in a batchwise or continuous manner. Batchwise production is preferred.

An almost quantitative conversion is obtained by the formation and precipitation of the aminotriazinone as its hydrogen chloride salt, combined with the formation of the ester of the displaced —COR$_4$ group.

In the practise of the present invention, compounds of formula I, for example 4-amino-6-methyl-3-oxo-2,3,4,5-tetrahydro-1,2,4-triazine hydrochloride, are prepared in high yield by the reaction of gaseous HCl with 6-methyl-4-acetylamino-4,5-dihydro-1,2,4-triazin-3-(2H)-one in methanol at around 45° C. The free 4-amino-6-methyl-3-oxo-2,3,4,5-tetrahydro-1,2,4-triazine can be obtained upon addition of an aqueous alkaline medium, e.g. NaOH.

The starting compounds of formula II are available commercially or can be prepared by known methods. Prior to the preparation of compounds of formula I, it is advantageous to prepare compounds of formula II in situ in the same or very similar alcoholic medium to that used in the process according to the invention, thus avoiding arduous isolation or separation steps.

The advantages of the process of the invention are as follows:

i) yields of up to 99% are obtained under optimised conditions;
ii) no side products are formed;
iii) improved volume yields are obtained;
iv) faster reaction times are achieved, and
v) there is negligible corrosion of the reaction vessel.

It is a further object of the present invention to provide a process for the preparation of a compound of formula III

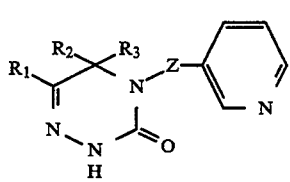

(III)

wherein $R_1$ is hydrogen, $C_1$-$C_{12}$alkyl, $C_3$-$C_6$cycloalkyl, $C_1$-$C_4$alkoxy-$C_1$-$C_6$alkyl, $C_1$-$C_2$haloalkyl, phenyl, benzyl, phenethyl, phenpropyl, phenbutyl, or phenpentyl, or a phenyl, benzyl, phenethyl, phenpropyl, phenbutyl or phenpentyl radical that is mono- or di-substituted by halogen, $C_1$-$C_5$alkyl, $C_1$-$C_2$haloalkyl, methoxy and/or ethoxy, $R_2$ is hydrogen, $C_1$-$C_6$alkyl or $C_3$-$C_6$cycloalkyl, or is phenyl that is unsubstituted or substituted by $C_1$-$C_{12}$alkyl, halogen or by $C_114$ $C_{12}$haloalkyl, or $R_1$ and $R_2$ together form a saturated or unsaturated 3- to 7-membered carbocycle, $R_3$ is hydrogen or $C_1$-$C_6$alkyl and Z is —N=CH— or —NH—CH$_2$—, which process comprises reacting an aminotriazinone of formula I

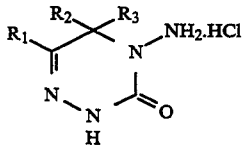

(I)

wherein $R_1$, $R_2$ and $R_3$ have the meanings above with an aldehyde of formula IV

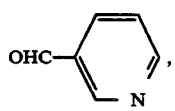

(IV)

and, if desired, converting the resulting pyridyl-methyleneamino-triazinone by selective reduction into pyridyl-methylamino-triazinone,
wherein the aminotriazinone of the formula I is prepared by the solvolysis of a compound of formula II

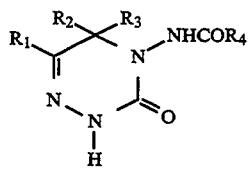

(II)

wherein $R_1$, $R_2$ and $R_3$ have the meanings given above and $R_4$ is H, $C_1$-$C_4$-alkyl, $C_3$-$C_6$-cycloalkyl, $C_1$-$C_4$-alkyl substituted by 1 to 9 chlorine atoms, $C_1$-$C_3$-alkoxy $C_1$-$C_3$-alkylthio, phenyl, pyridyl, or phenyl or pyridyl which is substituted with 1 to 3 substituents selected from the group of halogen, methyl, ethyl, methoxy, methylthio or nitro, in the presence of gaseous hydrogen chloride in an alcoholic medium.

Preferred compounds of the formula III are those wherein $R_1$ is hydrogen, $C_1$-$C_6$alkyl, $C_3$-$C_5$ cycloalkyl, phenyl or phenyl that is mono- or di-substituted by halogen, $C_1$-$C_3$alkyl, methoxy or ethoxy, each of $R_2$ and $R_3$ is hydrogen or $C_1$-$C_4$alkyl and Z is —N=CH— or —NH—CH$_2$—, more preferred are those compounds of the formula III wherein $R_1$ is hydrogen, $C_1$-$C_4$alkyl, cyclopropyl or phenyl; $R_2$ is hydrogen, methyl or ethyl; and $R_3$ is hydrogen or methyl; and Z is —N=CH— or —NH—CH$_2$—; most preferred is 6-methyl-4-(pyridin-3-yl-methyleneamino)-4,5-dihydro-1,2,4-triazin-3(2H)-one.

A preferred embodiment of the present invention is a process wherein the aldehyde of formula IV is prepared by the catalytic reduction of 3-cyanopyridine under hydrogen in the presence of Raney-nickel, characterised in that a) the Raney-nickel catalyst is present in an amount between 2 and 10 weight-% with respect to the cyanopyridine,
b) the solvent is aqueous carboxylic acid,
c) the pH is between 3.5 and 7,
d) the temperature is less than or equal to 40° C.,
e) the hydrogen pressure is between 0.2 and 5 bar,
f) the amount of hydrogen taken up is up to 110% with respect to the cyanopyridine, and
g) the amount of water present is in excess with respect to the cyanopyridine.

The process can be conducted continuously or batchwise. The amount of nicotinaldehyde in the aqueous medium is preferably 20 to 50 wt-%, more preferably 25 to 40 wt-%.

The Raney-nickel is present in an amount preferably between 3 and 7 wt-% with respect to the cyanopyridine. The Raney-nickel is stored under water prior to use.

The carboxylic acid can be present in stoichiometric or slightly sub-stoichiometric amounts or in excess with respect to the cyanopyridine. Stoichiometric amounts are preferred. Carboxylic acids form a buffer with ammonia. The pH rises quickly to about 5 during the course of the inventive process, and it is surprising that the reaction runs to completion at this pH without further addition of carboxylic acid. The pH may also be controlled by continuous addition of a carboxylic acid. Examples of aqueous carboxylic acid mixtures may contain an unlimited amount of $C_1$-$C_6$alcohols and a $C_1$-$C_6$carboxylic acid. The solvent is preferably aqueous acetic acid.

The temperature is preferably between 10° and 30° C., and more preferably between 20° and 30° C. The hydrogen pressure is preferably between 0.5 and 3 bar, more preferably between 0.5 and 1.5 bar. The water content with respect to the cyanopyridine is preferably up to 60% excess by weight, more preferably up to 40 wt-%. The reaction time is typically between 3 and 6 hours.

The following Examples demonstrate the process of the invention.

The aldehyde yield is determined by HPLC or gravimetrically by derivatisation with 4-amino-6-methyl-3-oxo-2,3,4,5-tetrahydro-1,2,4-triazine, abbreviated aminotriazinone.

EXAMPLE 1

Preparation of 4-amino-6-methyl-3-oxo-2,3,4,5-tetrahydro-1,2,4-triazine hydrochloride

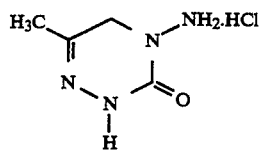

A suspension is prepared of 36.9 g (0.216 mol) 6-methyl-4-acetylamino-4,5-dihydro-1,2,4-triazin-3-(2H)-one in 115 g methanol (this suspension contains residual water from the solvent/educt corresponding to 0.25 mol water per mole acetyltriazinone). The suspension is heated to 45° C. and becomes a clear colourless solution. At between 45° and 50° C. a total of 11.8 g (0.324 mol) HCl are bubbled through this solution over a 2 to 3 hour period. After about 30% of the HCl has been added the reaction mixture is seeded with 4-amino-6-methyl-3-oxo-2,3,4,5-tetrahydro-1,2,4-triazine hydrochloride. Thereafter 4-amino-6-methyl-3-oxo-2,3,4,5-tetrahydro- 1,2,4-triazine precipitates out continuously as the hydrochloride salt. After about 2 hours stirring, the maximum conversion of 99% is reached, the mixture is cooled to between 10° and 13° C., filtered and dried. 34.0 g 4-amino-6-methyl-3-oxo-2,3,4,5-tetrahydro-1,2,4-triazine hydrochloride are isolated, representing a yield of 95.8% of theory.

EXAMPLE 2

Preparation of 4-amino-6-methyl-3-oxo-2,3,4,5-tetrahydro-1,2,4-triazine

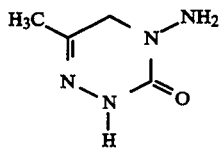

A suspension is prepared of 39.9 g (0.234 mol) 6-methyl-4-acetylamino-4,5-dihydro-1,2,4-triazin-3-(2H)-one in 99 g 95% methanol. The suspension is heated to 45° C. and becomes a clear colourless solution. At between 45° and 50° C. a total of 15.4 g (0.421 mol) HCl are bubbled through this solution over a 2 to 3 hour period. After about 30% of the HCl has been added the reaction mixture is seeded with 4-amino-6-methyl-3-oxo-2,3,4,5-tetrahydro-1,2,4-triazine hydrochloride. Thereafter 4-amino-6-methyl-3-oxo-2,3,4,5-tetrahydro-1,2,4,-triazine precipitates out continuously as the hydrochloride salt. After about 2 hours stirring, the maximum conversion of over 99% is reached. The reaction mixture is brought to pH 5 by the addition of 50% NaOH solution. The free aminotriazinone 4-amino-6-methyl-3-oxo-2,3,4,5-tetrahydro-1,2,4-triazine is formed in an amount of 29.7 g representing 14.3% by weight of the solution. This represents a yield of 99.2% of theory.

EXAMPLE 3

Comparison aqueous vs. gaseous HCl

A suspension is prepared of 6-methyl-4-acetylamino-4,5-dihydro-1,2,4-triazin-3-(2H)-one in methanol. The suspension is heated to 45° C. and becomes a clear colourless solution. At between 45° C. and 50° C. gaseous HCl (a) or aqueous HCl (b) is added to this solution over a 2 to 3 hour period. After about 30% of the gaseous HCl (a) or 50% of the aqueous HCl (b) has been added the reaction mixture is seeded with 4-amino-6-methyl-3-oxo-2,3,4,5-tetrahydro-1,2,4-triazine hydrochloride. Thereafter 4-amino-6-methyl-3-oxo-2,3,4,5-tetrahydro-1,2,4-triazine precipitates out continuously as the hydrochloride salt. After about 2 hours stirring, the maximum conversion is reached. The reaction mixture is brought to pH 5 by the addition of 50% NaOH solution, thereby forming free 4-amino-6-methyl-3-oxo-2,3,4,5-tetrahydro-1,2,4-triazine.

The respective yields of theory are as follows:

| Test No. | A [mol] | methanol [g] | gaseous HCl [g] | aqueous HCl [g] | yield of theory [%] |
| --- | --- | --- | --- | --- | --- |
| (a) | 0.234 | 99 | 15.4 | | 99.2 |
| (b) | 0.234 | 99 | | 41.6 | 77.2 |

A = 6-methyl-4-acetylamino-4,5-dihydro-1,2,4-triazin-3-(2H)-one

Test No. (a): This test is carried out with gaseous HCl. The maximum conversion is more than 99%. The free 4-amino-6-methyl-3-oxo-2,3,4,5-tetrahydro-1,2,4-triazine is formed in an amount of 29.7 g representing 14.3% by weight of the solution. This represents a yield of 99.2% of theory.

Test No. (b): Test (a) is repeated using aqueous HCl. The maximum conversion is 77.2%. The free 4-amino-6-methyl-3-oxo-2,3,4,5-tetrahydro-1,2,4-triazine is formed in an amount of 23.1 g representing 10.3% by weight of the solution. This represents a yield of 77.2% of theory.

EXAMPLE 4

(lab scale)

124.8 g 3-cyanopyridine, 277 g water and 72.2 g acetic acid are mixed together in a stirring autoclave. 14.6 g moist Raney-nickel (Ni contents about 60%) in 50 g water are added to the mixture which is then hydrogenated under a constant hydrogen pressure of 1 bar. When 110% of the theoretical hydrogen quantity have been taken up (after about 5 hours), the stirrer is switched off and the reaction mixture quenched with nitrogen. The catalyst is filtered off under an argon atmosphere and rinsed with water. 515 g product solution are obtained after filtration with 20.9% 3-pyridinaldehyde as determined by HPLC. This represents a yield of 85.2% of theory. The proportion of 3-picolylalcohol is 0.4% and that of 3-picolylamine 1.5%. The aldehyde yield is found to be 84% after derivatisation with aminotriazinone. The nickel loss of the catalyst is 115 mg, corresponding to ca. 1.3% of the total nickel content.

EXAMPLE 5

(pilot plant scale)

The procedure used in Example 3 is repeated except that 200 kg 3-cyanopyridine are used and corresponding amounts of the other reagents are added (a 1600-fold scale-up). After filtration 873 kg product solution are obtained with a 22.0% content of 3-pyridinaldehyde (yield 93.3% of theory). The 3-picolylamine content in the solution is 1.1% and that of 3-picolylalcohol 0.1%. The nickel loss from the catalyst is 0.5% of the total nickel content.

EXAMPLE 6

(at constant pH 5)

104 g 3-cyanopyridine and 200 g water are combined in a stirring autoclave. 12.1 g moist Raney-nickel (Ni contents about 60%) in 42 g water are added to the reaction mixture which is hydrogenated at room temperature under a constant hydrogen pressure of 1 bar. 191 g acetic acid are added in order to maintain a constant pH 5. When 110% of the theoretical hydrogen quantity has been taken up, the stirrer is switched off and the reaction mixture quenched with nitrogen. The catalyst is filtered off under an argon atmosphere and rinsed with water. After filtration there are obtained 561 g 3-pyridinaldehyde solution. The aldehyde yield is found to be 84% after derivatisation of 140.2 g of the solution with aminotriazinone. The nickel lost from the catalyst is 42 mg, corresponding to ca. 0.6% of the total nickel content.

EXAMPLE 7

(at 5 bar hydrogen pressure)

The procedure of Example 3 is followed except that the hydrogen pressure is maintained at a constant 5 bar. After filtration, a product solution is obtained with 14% 3-pyridinaldehyde as determined by HPLC, representing a yield of 64%. The aldehyde yield is 68% after derivatisation with aminotriazinone.

EXAMPLE 8

(at pH 4.7 to 7)

The procedure of Example 3 is followed except that 57.6 g acetic acid and 19.6 g sodium acetate are added. The aldehyde yield after derivatisation with aminotriazinone is 73%. The nickel lost from the catalyst is ca. 0.5% by weight of the total nickel content.

EXAMPLE 9

(concentration of 50% 3-cyanopyridine in water)

The procedure of Example 3 is followed except that 31.2 g 3-cyanopyridine and 31.2 g water are used. After derivatisation with aminotriazinone, the aldehyde yield is found to be 82%.

EXAMPLE 10

(catalyst recycled)

The procedure of Example 3 is repeated. When 110% of the theoretical amount of hydrogen have been taken up, the reaction is quenched with nitrogen and the hydrogenation solution filtered through a 0.5 μm sintered metal plate (surface area 4.5 cm²) at the reactor base. By addition of 3-cyanopyridine, water and acetic acid, the same catalyst is used as in Example 1 repeatedly. The aldehyde yield from the first three repeat cycles, in which the hydrogenation time is almost constant, is found to be 76% by derivatisation with aminotriazinone.

EXAMPLE 11

Preparation of 6-methyl-4-(pyridin-3-ylmethyleneamino)-4,5-dihydro-1,2,4-triazin-3(2H)-one To a suspension of 164 g of 4-amino-6-methyl-3-oxo-2,3,4,5-tetrahydro-1,2,4-triazine hydrochloride in 500 ml methanol a 50% NaOH solution is added until a pH of 6 is reached. Now 486 g of a solution containing 22% 3-pyridinaldehyde in water is added maintaining a temperature below 70° C. After the addition is completed the reaction mixture is kept at 65° C. for two hours. Then the suspension is cooled to about 5° C., filtered and dried to yield the title compound.

What is claimed is

1. A process for the preparation of a compound of formula III

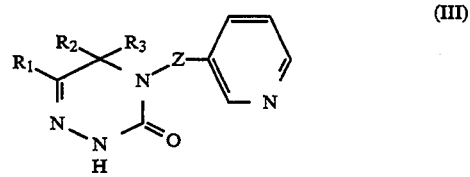

wherein $R_1$ is hydrogen, $C_1$–$C_{12}$alkyl, $C_3$–$C_6$cycloalkyl, $C_1$–$C_4$alkoxy-$C_1$–$C_6$alkyl, $C_1$–$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$haloalkyl, methoxy and/or ethoxy; $R_2$ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl; or $R_1$ and $R_2$ together form a saturated or unsaturated 3- to 7-membered carbocycle; $R_3$ is hydrogen or $C_1$–$C_6$alkyl and Z is —N=CH— or —NH—CH$_2$—, which process comprises reacting an aminotriazinone of formula I

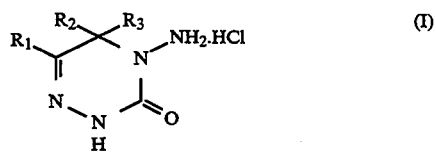

wherein $R_1$, $R_2$ and $R_3$ have the meanings above with an aldehyde of formula IV

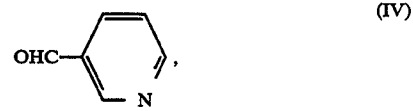

and, if desired, convening the resulting pyridyl-methyleneamino-triazinone by selective reduction into pyridyl-methylamino-triazinone, wherein the aminotriazinone of the formula I is prepared by the solvolysis of a compound of formula II

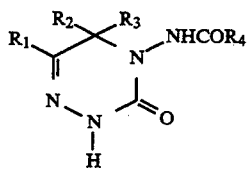

(II)

wherein R₁ is hydrogen, $C_1$–$C_{12}$alkyl, $C_3$–$C_6$cycloalkyl, $C_1$–$C_4$alkoxy-$C_1$–$C_6$alkyl, $C_1$–$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$haloalkyl, methoxy and/or ethoxy; R₂ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl; or R₁ and R₂ together form a saturated or unsaturated 3- to 7-membered carbocycle; R₃ is hydrogen or $C_1$–$C_6$alkyl; and R₄ is H, $C_1$–$C_4$-alkyl, $C_3$–$C_6$-cycloalkyl, $C_1$–$C_4$-alkyl substituted by 1 to 9 chlorine atoms, $C_1$–$C_3$-alkoxy, $C_1$–$C_3$-alkylthio, phenyl, pyridyl, or phenyl or pyridyl which is substituted with 1 to 3 substituents selected from the group of halogen, methyl, ethyl, methoxy, methylthio or nitro, in the presence of gaseous hydrogen chloride in an alcoholic medium.

2. A process according to claim 1 wherein R₁ is hydrogen, $C_1$–$C_6$alkyl, $C_3$–$C_5$cycloalkyl, phenyl or phenyl that is mono- or di-substituted by halogen, $C_1$–$C_3$alkyl, methoxy or ethoxy, each of R₂ and R₃ is hydrogen or $C_1$–$C_4$alkyl and Z is —N=CH— or —NH—CH₂—.

3. A process according to claim 2 wherein R₁ is hydrogen, $C_1$–$C_4$alkyl, cyclopropyl or phenyl; R₂ is hydrogen, methyl or ethyl; and R₃ is hydrogen or methyl; and Z is —N=CH— or —NH—CH₂—.

4. A process according to claim 3 wherein the compound of formula III is 6-methyl-4-(pyridin-3-ylmethyleneamino)-4,5-dihydro-1,2,4-triazin-3(2H)-one.

* * * * *